United States Patent [19]

Costanza et al.

[11] Patent Number: 4,470,966
[45] Date of Patent: Sep. 11, 1984

[54] CONTROLLED RELEASE INSECTICIDE COMPOSITION

[75] Inventors: John R. Costanza, North Plainfield, N.J.; Henry A. Terwedow, Jr., Glen Ellyn, Ill.

[73] Assignee: Celanese Corporation, New York, N.Y.

[21] Appl. No.: 358,125

[22] Filed: Mar. 15, 1982

[51] Int. Cl.³ ............................................. A01N 25/10
[52] U.S. Cl. ..................................................... 424/81
[58] Field of Search ......................................... 424/81

[56] References Cited

U.S. PATENT DOCUMENTS

| | | | |
|---|---|---|---|
| 4,145,439 | 3/1979 | Schulze et al. | 424/285 |
| 4,174,445 | 11/1979 | Mohring et al. | 544/223 |
| 4,220,663 | 9/1980 | Schulze et al. | 424/330 |
| 4,343,790 | 8/1982 | Pasarela | 424/81 |

*Primary Examiner*—Albert T. Meyers
*Assistant Examiner*—John Rollins
*Attorney, Agent, or Firm*—Scully, Scott, Murphy & Presser

[57] ABSTRACT

An emulsifiable concentrate of Imidan, an acrylic resin, a surfactant and a common organic solvent functions as a controlled release insecticide when applied to plant foliage.

8 Claims, No Drawings

4,470,966

CONTROLLED RELEASE INSECTICIDE COMPOSITION

BACKGROUND OF THE INVENTION

1. Field of the Invention

This invention relates to an insecticide composition. More particularly it relates to a controlled release foliar insecticide composition. This invention especially relates to a controlled release composition containing an organo thiophosphate insecticide, Imidan.

2. Description of the Prior Art

Foliar insecticides can be broadly classified by the manner in which they provide effective control. Some insecticides are toxic as contact poisons, e.g., they are lethal to insects by being brought in contact therewith as when an insect lights onto or crawls on foliage coated with the insecticide. Others prove lethal to insects as a stomach poison when the insect ingests insecticide-coated foliage.

The farmer's goal is to realize the highest possible return on his investment. Therefore, maximizing the yield of the marketable commodity is of prime concern. Apart from the proper use of fertilizers, adapted varieties and proper cultural practices, the farmer depends on crop protection chemicals to maximize yield. While the rationale for their use against weeds, diseases and insects is obvious, there are a number of associated disadvantages. These include such factors as toxicity, residuality, cost, resistance by pests, and weatherability. These factors are somewhat interrelated and in recent years, attempts have been made to deal with them.

Improving the efficiency of foliar insecticides can be achieved by reducing the application rates or by reducing the number of applications. The classical objective of controlled release technology is to extend the longevity of a pesticide thereby leading to decreased use and increased benefit to both the farmer and the consumer. Controlled release of a foliar insecticide is one effective means of reducing the per acre cost of the insecticide. Not only are the number of applications reduced but effectiveness of the insecticide is increased and undesirable side-effects to beneficial-insects often minimized.

Although the field of controlled release technology has been practiced for a number of years in the pharmaceutical industry, it is only recently that active interest has been displayed in the use of this technology for agricultural pesticides.

In one application, an interfacially polymerized microcapsule product containing methyl parathion has been utilized on cotton plants. In another, a laminate containing pesticide sandwiched between layers of plastic film has been applied to agricultural systems. (Proceedings of the Controlled Release Pesticide Symposium (1976).)

U.S. Pat. No. 3,212,967 to McFadden et al. discloses biocidally-active phosphorothioate esters which are polymerized with ethenoid monomers, such as acrylates, methacrylates and the like to form unitary polymeric molecules having the biocidal component temporarily held therein. The biocidal component is slowly released from the polymeric material in which it is entrapped when the materials are employed as film-forming coatings. These biocidally-active organic, polymeric materials are applied as aqueous latex dispersions or organic solvent solutions.

U.S. Pat. No. 3,592,910 to Clark et al. is directed to the use of liquid polyterpenes to protect pesticides against weathering and to extend the residual life of the pesticide. Pesticides, including insecticides, are controlled by release from these formulations. The polyterpene-containing composition may be applied to plants in undiluted condition, as a water emulsion or an organic solvent solution. This patent also states that acrylic polymers, vinyl-acrylic copolymers and other resins have been used as sticking agents for pesticides. However, no improved biological efficacy was reported for any of these compositions.

U.S. Pat. No. 2,767,194 to Fancher discloses a number of monothio and dithio-phosphates and their method of preparation. These products are useful as insecticides and acaracides. One particularly effective dithiophosphate is N-(mercaptomethyl) phthalimide S-(O,O-dimethyl phosphorodithioate) which is also known as Imidan.

Imidan is primarily used for the control of insects that attack commercial farm crops, especially fruit crops. The insects which are effectively controlled by Imidan includes alfalfa weevil, apple maggot, coddling moth, grape berrymoth, green apple aphid, Mexican bean beetle, oriental fruit moth, plum curculio, redbanded leafroller, rosy aphid and tobacco hornworm. The commercial cash crops treated with Imidan include such fruit crops as apples, apricots, cherries, grapes, nectarines, peaches, pears, plums and strawberries, as well as alfalfa, almonds, beans, citrus, corn, peas, pecans, potatoes, tobacco, rice and the like. Sales of Imidan in 1976 for use on apple orchards alone constituted over two million dollars and amounted to over four million dollars for use on all fruit crops.

Imidan is a white crystalline solid and is available commercially in technical grade purity of 94–96%. (All percentage figures herein are in terms of weight unless stated otherwise.) It is also available as a 50% active wettable powder. Imidan has been applied to cash crops as a foliar insecticide in the form of an aqueous spray. In this form, the adhesion to leaf surfaces, particularly if they are dirty or dusty, is not good and the weathering from rainfall requires repeated applications.

It is an object of the invention to increase the efficacy of Imidan by increasing its retention on leaf surfaces and increasing its weatherability, specifically against rainfall stress.

It is another object of this invention to provide Imidan in a controlled release formulation.

It is still another object of this invention to provide Imidan in a manner which reduces the frequency of application.

It is still a further object of this invention to provide a means of applying Imidan to foliar substrates whereby the runoff of the insecticide to the surrounding environment is substantially reduced.

SUMMARY OF THE INVENTION

In accordance with the present invention it has been found that Imidan can be provided as an emulsifable concentrate in a controlled release insecticide composition and that when applied to foliar substrates it is twice as efficacious as the conventional aqueous spray of wettable powder Imidan as a stomach poison insecticide both before and after rainfall. This controlled release Imidan composition is highly selective in that it functions as a stomach poison but not significantly as a contact poison whereas the conventionally applied aqueous spray of wettable powder functions in both fashions.

More particularly, this invention is directed to a controlled release insecticide composition comprising:

(a) an insecticidal effective amount of Imidan,
(b) an amount of acrylic resin effective to controllably release said Imidan,
(c) a surfactant, and
(d) a common organic solvent.

This invention is also directed to a method of controlling foliage eating or chewing insects susceptible to stomach poisons while leaving insects susceptible to contact poisons essentially unaffected which comprises applying these Imidan compositions of this invention to foliar substrates.

DESCRIPTION OF THE PREFERRED EMBODIMENTS

This invention relates to a controlled release formulation containing Imidan, an acrylic resin, a surfactant and a common organic solvent. By common organic solvent is meant an organic solvent in which the other components of the composition are soluble.

N-(mercaptomethyl)-phthalimide-S-(O,O-dimethyl phosphorodithioate) is a foliar insecticide. It is known as Imidan and also as Phosmet, Prolate and Appa. It will be referred to herein as Imidan. Imidan has the following structural formula:

$$\text{IMIDAN structure: bicyclic N-CH}_2\text{-S-P(=S)(OCH}_3)_2\text{ with two C=O groups}$$

IMIDAN

Imidan is a white crystalline powder and is available commercially as a technical grade product (94-96% purity). When practicing the present invention, Imidan is employed in its technical grade or in its pure crystalline form. In most instances the technical grade will be preferred because of its obvious economic advantage. Imidan in either form will act as a selective insecticide when utilizing the present invention since it will act as a stomach poison rather than as a contact poison. Although Imidan is available in a wettable powder formulation (50% active ingredient), this wettable powder does not provide the desired selectivity achieved with the present invention since it acts as both a stomach and a contact poison if substituted for the crystalline form or technical grade Imidan in the compositions of the present invention. Imidan in a wettable powder form does not constitute a useful insecticide in this invention.

The Imidan formulations of this invention provide insecticidal selectivity in that they do not have significant contact efficacy and thus do not affect, to a significant degree, beneficial or predator insects which provide such desirable effects as feeding on the harmful insects (praying mantis, ladybug, etc.) or pollinating flowering plants (honeybees, etc.). Such specificity of action is important in integrated pest management and minimizes one of the undesirable side-effects obtained from aqueous sprays of wettable powder Imidan. The reason for this difference in the contact poison effectiveness of the Imidan formulations of this invention vis-a-vis those prepared with Imidan wettable powder may be because the former forms a smooth continuous coating on the surface of a leaf whereas the wettable powder formulations form discontinuous discrete areas of high toxicant concentration. Apparently the smooth uniform, continuous film provided by the Imidan formulations of the invention actually protect the contact insect from the Imidan while either formulation proves lethal to those insects that chew or eat the coated foliage.

The acrylic resins which can be used herein can be selected from among the polymers and copolymers derived from the polymerization of alkyl acrylate monomer, alone or together with one or more other monomers copolymerizable therewith. The alkyl acrylate monomer is derived from the reaction of a monohydric alcohol, preferably of from 6 to about 18 carbon atoms, and more preferably, from 6 to 10 carbon atoms, with acrylic acid. Among the alkyl acrylates which are useful herein are included hexyl acrylate, octyl acrylate, decyl acrylate, dodecyl acrylate, 2-ethylhexyl acrylate, and the like. The foregoing monomers and mixtures thereof can be polymerized in accordance with known and conventional procedures and, as previously stated, can be interpolymerized with other copolymerizable monomers including alpha olefins such as ethylene, propylene or butylene; vinyl esters such as vinyl formate, vinyl acetate and vinyl butyrate; acrylamides and alkyl acrylamides such as methyl acrylamide, ethyl acrylamide and methyl methacrylamide; vinyl ethers such as methyl vinyl ether and t-butyl vinyl ether; vinyl ketones such as methyl vinyl ketone; dicarbonates such as diethyl fumarate and diethyl maleate; acid anhydrides such as maleic anhydride; and, styrene. Preferred copolymers include vinyl acetate/2-ethylhexyl acrylate and styrene/2-ethylhexyl acrylate. The precentage of acrylic/acrylate monomer(s) by weight which can be incorporated into useful acrylic resins according to this invention, can vary over a wide range and in general will range from a minimum of about 30% up to 100% of the weight of the polymer.

Typically, the acrylic resins will be incorporated into the insecticide emulsifiable concentrates employing a common organic solvent for the composition ingredients. By common organic solvent is meant an organic solvent or combination of organic solvents in which the ingredients, i.e., the Imidan, the acrylic resin and the surfactant, are soluble. Among the organic solvents which can be utilized for this purpose are included the aromatic hydrocarbons such as benzene, toluene and xylene; the halogenated, especially chlorinated, aromatic hydrocarbons such as the chlorobenzenes; ketones such as methylethylketone and acetone; and, esters such as ethyl acetate, propyl acetate, butyl acetate, ethyl propionate and ethyl butyrate. Combinations of these solvents may also be employed, particularly where any of the ingredients is insoluble or exhibits limited solubility in a single solvent.

A broad variety of surfactants can be employed with this invention. These surfactants aid in the emulsification of the compositions when they are added to water by providing adequate dispersion. They also provide enhanced wetting and sticking action so that the insecticide composition more readily adheres to the foliage of the plants. Suitable surfactants may be selected from the anionic, cationic and nonionic types including primary, secondary and tertiary alkyl amines, ethoxylated alcohol sulfates, alkyl sulfates, water soluble salts of a sulfonated alkyl, alkylbenezene, or alkyl glycerol ether, quaternary ammonium salts, quaternary imidazolinium salts, alkyl pyridinium salts, dialkyl morpholinium salts, ethoxylated fatty acids, sorbitol esters, alkylphenoxypoly (ethyleneoxy) ethanols, aromatic sulfonate-oxide condensates and the like. Preferred are the "Agrimuls" (Diamond Shamrock Corp.) which are a blend of anionic and nonionic aromatic sulfonate-oxide condensates and the "Igepals" (GAF Corporation) which are alkylphenoxypoly (ethyleneoxy) ethanols.

Fairly wide latitude in proportioning the amounts of Imidan insecticide, acrylic resin, solvent and surfactant in the emulsifable concentrates of this invention is permissable. The amount of Imidan must, of course, be sufficient to provide an insecticidal effective amount when the composition of the invention, diluted with water in its usual form of application, is applied to a foliar substrate. This amount will be dependent on the nature of the insects encountered, the degree of infestation and the nature of the plants to be treated. Regarding the acrylic resin, the amount present in the emulsifiable concentrates must be effective to controllably release the Imidan when the composition of the invention is in place on the plant foliage. In general, the Imidan insecticide can be present in an amount of from about 0.1 to about 50 percent by weight and preferably from about 1 to about 40 percent by weight. The acrylic resin can be incorporated in the concentrates so as to represent from about 0.5 to about 50 percent, and preferably from about 1 to about 30 percent, of the weight of the concentrate. The amount of solvent employed will depend primarily on the solvency of the particular solvent(s) selected for a particular acrylic resin, it being desired that there be essentially complete dissolution of the acrylic resin in the solvent of choice. Typically, from 1:1 to 10:1 weight parts of solvent per weight parts of acrylic resin can be employed. The solvent or solvent combination of choice must also provide dissolution of the remaining ingredients of the composition, i.e., the Imidan and the surfactant. With respect to surfactant, good results can be obtained using this component at from about 1 to about 10 percent by weight of the concentrate.

Although there is no criticality with respect to the sequence in which the aforesaid components are combined to prepare the concentrates, the acrylic resin will usually be dissolved in the solvent (unless the solvent was also used as the reaction medium in which the resin was prepared) and the resin solution will thereafter be mixed with the remaining ingredients.

The following examples illustrate embodiments of this invention.

In evaluating test formulations of the Imidan compositions, several bioassay procedures were utilized. These are described below:

A. Tobacco Hornworm (*Manduca sexta*)

Tobacco hornworm eggs were obtained from Carolina Biological Supply Company and reared on a modified Shorey pinto bean diet. Late 3rd and early 4th instar larvae were used in testing.

Tobacco plants grown in a greenhouse to a height of 40–80 cm. were used in the bioassay. The Imidan formulations were hand sprayed to run off on the leaf surfaces. The spraying apparatus was a DeVilbiss atomizer No. 152 with a No. 150 outlet tube and No. 115CP adjustable spray tip. The sprayer tip was held approximately 15 cm from the sprayed surface. The sprayed plant was then allowed to air dry.

Rainfall was simulated by a rainfall simulator apparatus. Plants left on this rain machine for 1 hr. received the equivalent of one inch of rainfall. These plants were subsequently air dried.

After drying, approximately 8 $cm^2$ of sprayed leaf were placed in a standard 100×15 mm plastic dish with one tobacco hornworm. This was replicated 15 to 20 times for each sample. After 48 hours the insects were examined for mortality or morbidity.

B. Mexican Bean Beetle (*Epilachna varivestis*)

A strain of Mexican bean beetle obtained from Boyce Thompson Institute, (BTI), Yonkers, N.Y. was maintained in colony. Both adults and larvae were reared solely on mammoth podded horticultural pole beans. This same variety of bean, 8 days post-planted, was used in the bioassay. Both the spraying and raining procedure are similar to that described in the tobacco hornworm bioassay. After drying, the plants were cut at the stem and tested. The sprayed bean cutting was placed in an 8-oz. Dixie cup. The stem protruded through a small hole in the bottom of the cup into a petri dish of water. Five beetle larvae were added to each plant and allowed to feed for 72 hr., after which mortality was scored.

C. Housefly (*Musca domestica*)

A colony of the USDA-Beltsville strain of houseflies was established. Immature flies were reared entirely on CSMA medium (Ralston Purina). A powdered milk and confectionary sugar mixture was the nutritional source for the adults. Only 24–72 hr. post-emerged adults were used for testing.

Initially, ivy plants were used in spraying Imidan formulations. Young tender leaves were picked the same day as the bioassay and sprayed as described for the tobacco plants. After drying, circular discs were punched from the sprayed leaves with a No. 10 cork borer. Four ivy punches from each spraying were taped to a petri dish lid and placed in a ½ gallon cardboard cylinder. Thereafter, twenty-five houseflies were introduced into the container and mortality was scored after 72 hours.

During cool weather, ivy was no longer available and McIntosh apples were substituted in the bioassay. Apples also provided a substrate of greater uniformity and realism than ivy leaves. The apples were sprayed to runoff as described above and placed in the ½ gallon cylinders with the flies.

EXAMPLE 1

A typical acrylic resin used in this invention, a polymer of vinyl acetate and 2-ethylhexyl acrylate, was prepared from the following ingredients:

|  | Wt. % |
| --- | --- |
| Vinyl acetate | 22.5 |
| 2-Ethylhexyl acrylate | 22.5 |
| Xylene | 45.0 |
| Ethyl acetate | 9.0 |
| Benzoyl peroxide | 1.0 |

The polymer was prepared as follows:
The two monomers and the xylene solvent were mixed together to form Fraction A. The benzoyl peroxide was dissolved in the ethyl acetate and identified as Fraction B.

300 ml of Fraction A and 40 ml of Franction B were placed in a 2 liter flask equipped with a reflux condenser and a stirrer. The contents of the flask were heated under reflux for a period of 1 ½ hours during which additional quantities of Fraction A and Fraction B were added to the flask. Heating under reflux was continued for an additional 3-4 hours. The contents of the flask constituted a solution of vinyl acetate/2-ethylhexyl acrylate polymer.

In a similar fashion other polymer solutions were prepared from these and other monomers including: acrylic acid, methyl methacrylate, N-vinyl pyrrolidone and styrene.

Formulations of the present invention were prepared as emulsifiable concentrates as follows:

Technical Imidan was dissolved in a suitable solvent at concentrations ranging from 10-25 weight percent. The polymer solution and surfactant were then added. Alternately, the technical Imidan was added to a mixture of polymer solution and surfactant and tumbled overnight. If the Imidan did not dissolve, then additional quantities of solvent were added. The latter technique utilized the solvent in the polymer solution to dissolve the Imidan, thereby eliminating the need and cost of additional solvent.

Typical Imidan formulations of this type are shown in Table I below:

TABLE I

| COMPONENT | % RANGE |
|---|---|
| Imidan (Technical) | 10-25 |
| Polymer Solution | 38-88 |
| Surfactant | 1-10 |
| Xylene* | 10-50 |

*Required when less polymer solution was used in order to obtain a fluid composition.

EXAMPLE 2

A number of emulsifiable concentrates were prepared as described above utilizing several different polymer solutions of varying compositions. The polymer solutions were prepared in the fashion described in Example 1. Each concentrate was diluted with water to a uniform Imidan concentration of 500 ppm. These aqueous compositions together with a control of Imidan wettable powder containing 50% active ingredient (designated herein as Imidan 50 WP) also diluted in water to a 500 ppm Imidan concentration, were evaluated for efficacy against tobacco hornworms on tobacco in accordance with the bioassay described above.

The formulation used in these screening tests is listed in Table II below and the results obtained are presented in Table III below.

TABLE II

| IMIDAN SCREENING FORMULATIONS | |
|---|---|
| COMPONENT | WEIGHT % |
| Polymer Solution | 32.3 |
| Imidan (Technical)(a) | 16.1 |
| Agrimul A-300(b) | 1.6 |
| Agrimul N-300(b) | 1.6 |
| Xylene | 48.4 |

(a)96.4% Active
(b)Surfactants (nonionic, anionic blend)

TABLE III

| EFFICACY OF IMIDAN COMPOSITIONS AND IMIDAN 50 WP | | | | |
|---|---|---|---|---|
| | (AGAINST TOBACCO HORNWORM) PERCENT TOBACCO HORNWORM MORTALITY(*) | | | |
| POLYMER | WITHOUT RAIN | | WITH RAIN | |
| COMPOSITION | 24 HRS. | 48 HRS. | 24 HRS. | 48 HRS. |
| VAc/2-EHA | 100 | 100 | 60 | 80 |
| VAc/2-EHA/AA | 67 | 100 | 47 | 60 |
| VAc/2-EHA/NVP | — | 67 | — | 27 |
| MMA/2-EHA | 60 | 73 | 6 | 13 |
| MMA/2-EHA/AA | 60 | 73 | 0 | 0 |
| MMA/2-EHA/NVP | — | 80 | — | 13 |
| STY/2-EHA | 40 | 40 | 13 | 40 |
| STY/2-EHA/AA | 87 | 93 | 27 | 33 |
| STY/2-EHA/NVP | — | 100 | — | 27 |
| IMIDAN 50WP | — | 93 | — | 33 |

Notes:
(*) At 500 PPM Imidan on tobacco plants.
VAc = vinyl acetate
2-EHA = 2-ethylhexyl acrylate
AA = acrylic acid
NVP = N—vinyl pyrrolidone
MMA = methyl methacrylate
STY = styrene Based on these screening tests, the VAc/2-EHA polymer was selected for further evaluation. Four emulsifiable Imidan concentrates containing this polymer were prepared. Their compositions are shown in Table IV below.

TABLE IV

| IMIDAN COMPOSITIONS CONTAINING VAc/2-EHA | | | | |
|---|---|---|---|---|
| | Weight % | | | |
| Component | IV-1 | IV-2 | IV-3 | IV-4 |
| VAc/2-EHA Solution(a) | 82.5 | 80.9 | 88.0 | 86.5 |
| Imidan (Technical) | 16.5 | 16.2 | 11.0 | 10.8 |
| Surfactant(b) | 1.0 | 2.9 | 1.0 | 2.7 |
| | 100.0 | 100.0 | 100.0 | 100.0 |

(a)45% polymer in xylene
(b)1:1 mixture of Agrimul A-300 and N-300

Each of these formulations and Imidan 50 WP were diluted in water to a 500 ppm Imidan concentration and evaluated in the tobacco hornworm bioassay. The results are presented in Table V below.

TABLE V

| BIOEVALUATION OF IMIDAN COMPOSITIONS (AGAINST TOBACCO HORNWORMS) | | |
|---|---|---|
| | PERCENT TOBACCO HORNWORM MORTALITY(a) | |
| Sample | Without Rain | With Rain(b) |
| IV-1 | 100 | 40 |
| IV-2 | 93 | 67 |
| IV-3 | 100 | 33 |
| IV-4 | 93 | 93 |
| Imidan 50WP | 67 | 27 |

(a)At 500 ppm, after 48 hours.
(b)1 inch rain

All the Imidan emulsifiable concentrates of the invention had good efficacy against tobacco hornworm without rain, being significantly better than the wettable powder Imidan. However, after one inch of rainfall, Samples IV-2 and IV-4 were still significantly more efficacious. These two compositions had the highest surfactant to insecticide ratio.

Samples IV-2 and IV-4 were compared with Imidan 50 WP in a dose-response evaluation. These results are shown in Table VI below:

TABLE VI

DOSE-RESPONSE INVESTIGATION OF IMIDAN COMPOSITIONS (AGAINST TOBACCO HORNWORMS)

| SAMPLE | CONCENTRATION PPM ACTIVE IMIDAN | PERCENT TOBACCO HORNWORM MORTALITY WITHOUT RAIN | RAIN |
|---|---|---|---|
| Imidan 50WP | 1000 | 100 | 40 |
| | 500 | 73 | 13 |
| | 250 | 27 | 0 |
| | 125 | 7 | 0 |
| IV-4 | 1000 | 100 | 60 |
| | 500 | 100 | 47 |
| | 250 | 73 | 7 |
| | 125 | 0 | 7 |
| IV-2 | 1000 | 100 | 33 |
| | 500 | 80 | 27 |
| | 250 | 27 | 0 |
| | 125 | 13 | 7 |

These data show that Sample IV-4 was superior in efficacy to Sample IV-2. These data also indicate that Sample IV-4 was effective against tobacco hornworms after rainfall at half the concentration of Imidan 50 WP.

EXAMPLE 3

The emulsifiable concentrates of this invention were evaluated against Mexican bean beetles. Two polymer solutions were used-STY/2-EHA and VAc/2-EHA. The composition of these concentrates is shown in Table VII below.

TABLE VII

IMIDAN COMPOSITIONS FOR USE AGAINST MEXICAN BEAN BEETLES

| COMPONENT | COMPOSITION (%) VII-1 | VII-2 |
|---|---|---|
| STY/2-EHA Solution[a] | 79.3 | — |
| VAc/2-EHA Solution[a] | — | 79.3 |
| IMIDAN (Technical) | 10.6 | 10.6 |
| SURFACTANT[b] | 10.1 | 10.1 |

[a]45% polymer in xylene
[b]Igepal CO 630, Nonylphenoxypoly(ethyleneoxy)ethanol

The STY/2-EHA solution polymer, being relatively hydrophobic, would be expected to adhere better to hydrophobic surfaces and to provide better rain resistance. The VAc/2-EHA solution polymer, being more hydrophilic, would be expected to have better water dispersing properties but poorer rain resistance. The hydrophilic or hydrophobic nature of the polymer could also influence the diffusion of the Imidan from the coating into the leaf.

The results of the dose-response tests with these compositions and Imidan 50 WP when evaluated in the Mexican bean beetle bioassay are shown in Table VIII below.

TABLE VIII

BIOEVALUATION OF IMIDAN COMPOSITIONS (AGAINST MEXICAN BEAN BEETLE)

| SAMPLE | CONCENTRATION (PPM) | PERCENT BEETLE MORTALITY WITHOUT RAIN | WITH RAIN |
|---|---|---|---|
| VII-1 | 1000 | 100 | 100 |
| (STY/2-EHA) | 500 | 100 | 100 |
| | 250 | 100 | 90 |
| | 125 | 100 | 74 |
| | 62.5 | 93 | 62 |
| VII-2 | 1000 | 100 | 96 |
| (VAc/2-EHA) | 500 | 100 | 55 |
| | 250 | 100 | 60 |
| | 125 | 100 | 42 |
| | 62.5 | 86 | 26 |
| IMIDAN 50WP | 1000 | 100 | 97 |
| | 500 | 100 | 83 |
| | 250 | 97 | 67 |
| | 125 | 90 | 37 |
| | 62.5 | 37 | 15 |

These data show that without rainfall both samples were twice as effective as Imidan 50 WP (compare VII-1 and VII-2 at 62.5 ppm with Imidan 50 WP at 125 ppm). However, after rainfall only the more hydrophobic polymer, Sample VII-1, retained twice the effectiveness of the Imidan 50 WP. The more hydrophilic polymer, Sample VII-2, had efficacy approximately equal to the Imidan 50 WP after rainfall.

EXAMPLE 4

The emulsifiable concentrates of the invention and Imidan 50 WP were evaluated as contact insecticides against houseflies.

The compositions previously found to be effective against the tobacco hornworm and the Mexican bean beetle were evaluated against houseflies. The results of the housefly bioassay on ivy and apples are shown in Table IX below.

TABLE IX

HOUSEFLY BIOASSAY WITH IMIDAN COMPOSITIONS ON APPLES AND IVY

| SAMPLE IDENTIFICATION | PERCENT HOUSEFLY MORTALITY (500 PPM) IVY | APPLES |
|---|---|---|
| IV-2 | 4 | 0 |
| IV-4 | 8 | 0 |
| VII-1 | 0 | 0 |
| IMIDAN 50WP | 60 | 84 |

The poor results for the compositions of the invention were unexpected in view of the successes as a stomach poison. These data show that there is an almost complete lack of efficacy of the controlled release Imidan compositions against the housefly bioassay contact system.

It appears that the compositions of this invention function as stomach poisons but do not have any significant contact efficacy. It also appears that by the incorporation of a polymer into an Imidan system, a composition of greater insecticidal selectivity is obtained.

What is claimed is:

1. A controlled release insecticide composition in the form of an emulsifiable concentrate which consists essentially of:
   (a) an insecticidal effective amount of Imidan,
   (b) an amount of acrylic resin effective to controllably release said Imidan, said acrylic resin comprising 30 to 100 wt. % of a $C_6$–$C_{18}$ alkyl acrylate monomer,
   (c) an effective amount of a surfactant capable of aiding in the water emulsification of the composition and enhancing the wetting and sticking action of the composition, and (d) an effective amount of a common organic solvent in which said Imidan, said acrylic resin and said surfactant are dissolved.

2. An insecticide composition according to claim 1 wherein the acrylic resin is a copolymer of vinyl acetate and 2-ethylhexyl acrylate.

3. An insecticide composition according to claim 1 wherein the acrylic resin is a copolymer of styrene and 2-ethylhexyl acrylate.

4. An insecticide composition according to claim 1 wherein the common organic solvent is xylene.

5. An insecticide composition according to claim 1 wherein the surfactant is aromatic sulfonate-oxide condensates or alkylphenoxypoly (ethyleneoxy) ethanols.

6. An insecticide composition according to claim 1 wherein Imidan comprises about 1 to about 40% of the composition, the acrylic resin comprises about 1 to about 30% of the composition, the surfactant comprises about 1 to about 10% of the composition and the weight ratio of solvent to acrylic resin is from 1:1 to 10:1.

7. A method of controlling foliage eating or chewing insects susceptible to stomach poisons while leaving insects susceptible to contact poisons essentially unaffected which comprises:

applying to a foliar substrate an effective amount of the insecticide composition of claim 1.

8. A method of controlling foliage eating or chewing insects susceptible to stomach poisons while leaving insects susceptible to contact poisons essentially unaffected which comprises:

applying to a foliar substrate an effective amount of the insecticide composition of claims 2, 3, 4, 5 or 6.

* * * * *